United States Patent
Foessel

(10) Patent No.: US 6,890,887 B2
(45) Date of Patent: May 10, 2005

(54) SYNERGISTIC HERBICIDAL METHODS AND COMPOSITIONS COMPRISING DINITROANILINE AND IMIDAZOLINONE COMPOUNDS

(75) Inventor: Pascal Foessel, Tassin la Demi Lune (FR)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/692,817

(22) Filed: Oct. 27, 2003

(65) Prior Publication Data

US 2004/0116295 A1 Jun. 17, 2004

Related U.S. Application Data

(63) Continuation of application No. 09/542,614, filed on Apr. 4, 2000, now Pat. No. 6,673,748.

(30) Foreign Application Priority Data

Apr. 9, 1999 (FR) .............................. 99 04486

(51) Int. Cl.$^7$ .......................... A01N 33/18; A01N 43/48
(52) U.S. Cl. ........................ 504/139; 504/253; 504/347
(58) Field of Search ................................ 504/139, 253, 504/347

(56) References Cited

U.S. PATENT DOCUMENTS

| 4,822,405 A | * | 4/1989 | Martin et al. ................ 504/130 |
| 5,393,731 A | * | 2/1995 | Kimler et al. ............... 504/139 |
| 5,624,884 A | * | 4/1997 | Morgan et al. ............. 504/148 |

OTHER PUBLICATIONS

Klingman et al. Weed Science: Principles and Practices. 2nd ed. John Wiley & Sons:NY. p. 418–421. 1982.*
Anderson, Wood Powell. Weed Science: Principles and Applications. 3rd ed. West Pub. Co.:NY. p. 200–204. 1996.*

* cited by examiner

Primary Examiner—S. Mark Clardy
(74) Attorney, Agent, or Firm—Novak Druce & Quigg, LLP

(57) ABSTRACT

The present invention provides a method for the synergistic control of undesirable plants such as *Poa, Polygonum* and *Setaria* which comprises applying to the plants or their locus a synergistically effective amount of a combination of a dinitroaniline compound and an imidazolinone compound. Further provided are synergistic herbicidal compositions comprising dinitroaniline and imidazolinone compounds.

12 Claims, No Drawings

SYNERGISTIC HERBICIDAL METHODS AND COMPOSITIONS COMPRISING DINITROANILINE AND IMIDAZOLINONE COMPOUNDS

This is a continuation of application Ser. No. 09/542,614, filed Apr. 4, 2000 now U.S. Pat. No. 6,673,748

BACKGROUND OF THE INVENTION

Certain weeds such as *Poa, Polygonum* and *Setaria* are particularly difficult to control. Their full-season competition can reduce crop yields and cause significant economic loss in crop production. Accordingly, a need exists in the art for an improved method for the control of these undesirable plants.

SUMMARY OF THE INVENTION

Surprisingly, it has now been found that the combination of a dinitroaniline compound with an imidazolinone compound provides synergistic weed control. In particular, the synergistic herbicidal methods and compositions of this invention provide improved control of pestiferous weeds such as *Poa, Polygonum* and *Setaria*.

The present invention provides a method for the synergistic control of undesirable plants such as *Poa, Polygonum* and *Setaria* which comprises applying to the locus of said plants, to the foliage or stems of said plants, or to the soil or water containing seeds of said plants a synergistically effective amount of a combination of a dinitroaniline compound selected from the group consisting of pendimethalin, trifluralin, benfluralin, butralin, dinitramine, ethalfluralin, fluazinam, fluchloralin, flumetralin, oryzalin and prodiamine; and at least one imidazolinone compound selected from the group consisting of imazamox, the R isomer thereof or a salt thereof; imazethapyr, the R isomer thereof or a salt thereof; imazaquin, the R isomer thereof or a salt thereof; imazapic, the R isomer thereof or a salt thereof; and imazapyr, the R isomer thereof or a salt thereof; and mixtures thereof.

The present invention also provides a synergistic herbicidal composition which comprises an agriculturally acceptable carrier and a synergistically effective amount of a combination of a dinitroaniline compound selected from the group consisting of pendimethalin, trifluralin, benfluralin, butralin, dinitramine, ethalfluralin, fluazinam, fluchloralin, flumetralin, oryzalin and prodiamine; and at least one imidazolinone compound selected from the group consisting of imazamox, the R isomer thereof or a salt thereof; imazethapyr, the R isomer thereof or a salt thereof; imazaquin, the R isomer thereof or a salt thereof; imazapic, the R isomer thereof or a salt thereof; imazapyr, the R isomer thereof or a salt thereof; and mixtures thereof.

DETAILED DESCRIPTION OF THE INVENTION

Surprisingly, it has now been found that the application of a combination of a dinitroaniline compound plus at least one imidazolinone compound provides synergistic control of troublesome weeds, particularly *Poa, Polygonum* and *Setaria*. That is, the application of the combination of the invention gives a mutual reinforcing action such that the application rates of the individual herbicidal components can be reduced and still the same herbicidal effect is achieved or, alternatively, the application of the combination of herbicidal components demonstrates a greater herbicidal effect than expected from the effect of the application of the individual herbicidal components when applied singly at the rate at which they are present in the combination (synergistic effect).

As used in the specification and claims, the terms used for the imidazolinone compounds imazamox, imazethapyr, imazaquin, imazapic and imazapyr designate the compound, the R isomer thereof, or the agriculturally acceptable salt thereof. The imidazolinone compounds and their corresponding chemical names are listed herein below.

Imazamox designates 2-(4-isopropyl-4-methyl-5-oxo-2-imidazolin-2-yl)-5-(methoxymethyl)nicotinic acid, the R isomer thereof, a salt thereof, or mixtures thereof.

Imazethapyr designates 5-ethyl-2-(4-isopropyl-4-methyl-5-oxo-2-imidazolin-2-yl)nicotinic acid, the R isomer thereof, a salt thereof, or mixtures thereof.

Imazaquin designates 2-(4-isopropyl-4-methyl-5-oxo-2-imidazolin-2-yl)quinolinecarboxylic acid, the R isomer thereof, a salt thereof, or mixtures thereof.

Imazapic designates 2-(4-isopropyl-5-methyl-5-oxo-2-imidazolin-2-yl)-5-methylnicotinic acid, the R isomer thereof, a salt thereof, or mixtures thereof.

Imazapyr designates 2-(4-isopropyl-4-methyl-5-oxo-2-imidazolin-2-yl)nicotinic acid, the R isomer thereof, a salt thereof, or mixtures thereof.

In the context of the present invention, the term agriculturally acceptable salt includes alkali metal, ammonium, alkyl sulphonium or alkylphosphonium salt or the quaternary salt of an amine having a molecular weight of less than 300. In particular, the term includes isopropylammonium, ammonium, sodium and trimesium, especially isopropylammonium and ammonium.

As used in the specification and claims, the term R isomer designates the optical isomer of an imidazolinone compound having the R configuration assigned to the assymetric carbon in the imidazolinone ring which is substituted by a methyl and an isopropyl group, for example the R isomer of the imidazolinone compound imazapyr is shown below.

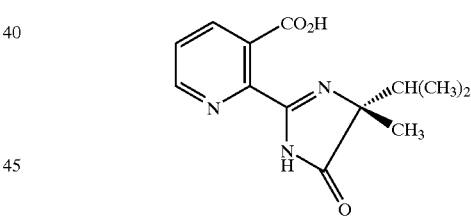

In accordance with the method of the invention, a synergistically effective amount of a combination of a dinitroaniline compound, preferably pendimethalin, and at least one imidazolinone compound, preferably imazamox, is applied to the locus of the undesirable plants, the foliage or stems of the undesirable plants or the soil or water containing seeds of the undesirable plants, particularly plants selected from the genera *Poa, Polygonum* and *Setaria*, preferably *Poa annua, Polygonum persicaria* and *Setaria verticilliata*. Advantageously, synergistic control of undesirable plant species is achieved from either preemergence or postemergence application of the dinitroaniline and imidazolinone compounds.

Preferred combinations of the invention are those combinations wherein the weight/weight (wt/wt) ratio of dinitroaniline compound:imidazolinone compound is about 10:3 to 900:1. More preferred combinations of the invention are combinations of pendimethalin and an imidazolinone compound wherein the wt/wt ratio of pendimethalin:imidazolinone compound is about 10:3 to 900:1. Most preferred combinations of this invention are combinations of pendimethalin and imazamox wherein the wt/wt ratio of pendimethalin:imazamox is about 20:3 to 100:1.

The synergistically effective amount of the combination of a dinitroaniline compound and an imidazolinone compound may vary according to prevailing conditions such as the particular dinitroaniline and imidazolinone compounds present, weed pressure, application timing, weather conditions, soil conditions, mode of application, topographical character, target crop species, and the like. In general, a synergistic effect may be achieved at application rates of about 500 g/ha to 4,500 g/ha of a dinitroaniline compound in combination with about 5 g/ha to 150 g/ha of an imidazolinone compound, preferably about 500 g/ha to 4,500 g/ha of pendimethalin in combination with about 15 g/ha to 100 g/ha of imazamox.

The present invention also provides a synergistic herbicidal composition comprising an agriculturally acceptable carrier and a synergistically effective amount of a combination of a dinitroaniline compound and at least one imidazolinone compound. The agriculturally acceptable carrier may be a solid or a liquid. While not required, the combination composition of the invention may also contain other additives such as fertilizers, inert formulation aids, e.g. surfactants, emulsifiers, defoamers, dyes, extenders and the like.

Compositions according to the invention may be formulated in any conventional form, for example in the form of a twin pack, or as an emulsifiable concentrate, soluble granular, dispersible granular and the like with emulsifiable concentrates being preferred.

Preferred compositions of the invention are those compositions wherein the dinitroaniline and imidazolinone compounds are present in a wt/wt ratio of about 10:3 to 900:1 dinitroaniline compound:imidazolinone compound. More preferred inventive compositions are those compositions wherein the dinitroaniline compound is pendimethalin and the imidazolinone compound is imazamox and the wt/wt ratio is about 20:3 to 100:1 pendimethalin:imazamox.

In actual practice, a tank mix of a commercially convenient association or presentation of a dinitroaniline compound and an imidazolinone compound may be applied to the locus of the undesirable plants, to the foliage or stems of the undesirable plants or to the soil or water containing seeds of the undesirable plants, or the dinitroaniline compound and imidazolinone compound may be applied separately or sequentially, or the combination compositions of the invention may be applied in a single combined form as described hereinabove.

The synergistically effective amount of a combination of a dinitroaniline compound and an imidazolinone compound suitable for use in the composition of the invention is that amount sufficient to provide about 500 g/ha to 4,500 g/ha of a dinitroaniline compound and about 5 g/ha to 150 g/ha of an imidazolinone compound, preferably about 500 g/ha to 4,500 g/ha of pendimethalin and about 15 g/ha to 100 g/ha of imazamox, more preferably about 500 g/ha to 1,500 g/ha of pendimethalin and about 15 g/ha to 75 g/ha of imazamox.

The synergistic herbicidal compositions of the invention provide effective resistance management programs in crop production, for example peas, soybeans or other legumes or imdazolinone-resistant/tolerant crops such as corn, canola, sugarbeet, wheat, rice, soybean and the like crop production, preferably legumes (especially peas) or imidazolinone-resistant/tolerant corn crop production.

For a more clear understanding of the invention, specific examples thereof are set forth below. These examples are merely illustrative, and are not to be understood as limiting the scope and underlying principles of the invention in any way.

In the following examples, synergism is determined by the Colby[1] method, i.e. the expected (or predicted) response of the combination is calculated by taking the product of the observed response for each individual component of the combination when applied alone divided by 100 and subtracting this value from the sum of the observed response for each component when applied alone. Synergism of the combination is then determined by comparing the observed response of the combination to the expected (or predicted) response as calculated from the observed response of each individual component alone.

[1] Colby, S. R., Weeds, 1967 (15), p. 20–22

The foregoing is illustrated mathematically below, wherein a combination, C, is composed of component A plus component B and Obs. designates the observed response of the combination C.

$$(A + B) - \frac{AB}{100} = \text{Expected response (Exp.)}$$

$$\text{Synergism} \equiv (\text{Obs.} - \text{Exp.}) > 0$$

EXAMPLE 1

Evaluation of the Herbicidal Activity of a Combination of Pendimethalin and Imazamox Formulations containing imazamox[1], pendimethalin[2] and an imazamox/pendimethalin combination[3] are diluted with water and applied preemergence at volumes of 200 L/ha to 400 L/ha to field plots to provide the rates shown in Table I. 60 days after application, the plots are visually evaluted for percent weed control. The results are summarized in Table I. If more than one plot is included in an evaluation, the results are averaged.

[1] BOLERO® 40 SL, an imazamox aqueous concentrate commercially available from American Cyanamid Company, Parsippany, N.J.
[2] STOMP® 400 SC, a pendimethalin suspension concentrate commercially available from American Cyanamid Company, Parsippany, N.J.
[3] An emulsifiable concentrate containing imazamox and pendimethalin.

As can be seen from the data in Table I, application of a combination of pendimethalin plus imazamox gives greater control of *Poa annua, Polygonum persicaria* and *Setaria verticilliata* than that which could be predicted from the weed control resulting from the application of either pendimethalin or imazamox alone.

TABLE I

Evaluation of Weed Control

| Weed Species | Imazamox g/ha | Pendi-methalin g/ha | % Weed Control | | |
|---|---|---|---|---|---|
| | | | Observed | Expected | (Obs. – Exp.) |
| *Poa annua* | 0 | 1,125 | 63 | — | |
| | 75 | 0 | 68 | — | |
| | 75 | 1,125 | 97 | 88 | 9 |
| *Polygonum persicaria* | 0 | 1,125 | 76 | — | |
| | 75 | 0 | 66 | — | |
| | 75 | 1,125 | 100 | 92 | 8 |
| *Setaria verticilliata* | 0 | 1,125 | 86 | — | |
| | 75 | 0 | 45 | — | |
| | 75 | 1,125 | 96 | 92 | 4 |

What is claimed is:

1. A method for the synergistic control of undesirable *Poa, Polygonum* or *Setaria* plants which comprises applying to the locus of said plants, to the foliage or stems of said plants or to the soil or water containing seeds of said plants a synergistically effective amount of a combination of a dinitroaniline compound selected from the group consisting of pendimethalin, trifluralin, benfluralin, butralin, dinitramine, ethalfluralin, fluazinam, fluchloralin, flumetralin, oryzalin and prodiamine: and an imidazolinone compound selected from the group consisting of R-imazamox, R-imazethapyr, R-imazaquin, R-imazapic, R-imazapyr or the agriculturally acceptable salts thereof, and mixtures thereof.

2. The method according to claim 1 conducted in the presence of imidazolinone-resistant/tolerant crops.

3. The method according to claim 1 conducted in the presence of imidazolinone-resistant/tolerant corn, canola, sugarbeet, wheat, rice or soybean.

4. The method according to claim 1 wherein the dinitroaniline compound and imidazolinone compound are present at a wt/wt ratio of about 10:3 to 900:1.

5. The method according to claim 1 wherein the synergistically effective amount is about 500 g/ha to 4,500 g/ha of a dinitroaniline compound and about 5 g/ha to 150 g/ha of an imidazolinone compound.

6. The method according to claim 1 wherein said plants are *Poa annua, Polygonum persicaria* or *Setaria verticillata*.

7. The method according to claim 6 wherein said plants are *Poa annua* or *Polygonum persicaria*.

8. The method according to claim 1 wherein the dinitroaniline compound and imidazolinone compound are present at a wt/wt ratio of about 20:3 to 100:1.

9. The method according to claim 8, wherein said plants are *Poa annua* or *Polygonum persicaria*.

10. The method according to claim 9, wherein the synergistically effective amount is about 500 g/ha to 4,500 g/ha of the dinitroaniline compound and about 15 g/ha to 100 g/ha of the imidazolinone compound.

11. A herbicidal composition for the synergistic control of undesirable *Poa, Polygonum* or *Setaria* plants which composition comprises an agriculturally acceptable carrier and a synergistically effective amount of a combination of a dinitroaniline compound selected from the group consisting of pendimethalin, trifluralin, benfluralin, butralin, dinitramine, ethalfluralin, fluazinam, fluchloralin, flumetralin, oryzalin and prodiamine; and an imidazolinone compound selected from the group consisting of R-imazamox, R-imazethapyr, R-imazaquin, R-imazapic R-imazapyr or the agriculturally acceptable salts thereof, and mixtures thereof.

12. The composition according to claim 11 wherein the dinitroaniline compound and imidazolinone compound are present at a wt/wt ratio of about 10:3 to 900:1.

* * * * *